(12) United States Patent
Tredinnick et al.

(10) Patent No.: US 10,682,195 B2
(45) Date of Patent: Jun. 16, 2020

(54) SURGICAL GUIDE

(71) Applicant: OSSABILITY LIMITED, Christchurch (NZ)

(72) Inventors: Seamus John Tredinnick, Christchurch (NZ); Brent Michael Higgins, Christchurch (NZ)

( * ) Notice: Subject to any disclaimer, the term of this patent is extended or adjusted under 35 U.S.C. 154(b) by 220 days.

(21) Appl. No.: 15/548,966

(22) PCT Filed: Feb. 5, 2016

(86) PCT No.: PCT/NZ2016/050009
§ 371 (c)(1),
(2) Date: Aug. 4, 2017

(87) PCT Pub. No.: WO2016/126168
PCT Pub. Date: Aug. 11, 2016

(65) Prior Publication Data
US 2018/0028272 A1 Feb. 1, 2018

(30) Foreign Application Priority Data
Feb. 5, 2015 (NZ) ........................................ 704592

(51) Int. Cl.
*A61B 17/15* (2006.01)
*A61B 17/17* (2006.01)
(Continued)

(52) U.S. Cl.
CPC ............ *A61B 90/11* (2016.02); *A61B 17/151* (2013.01); *A61B 17/1764* (2013.01);
(Continued)

(58) Field of Classification Search
CPC ............................ A61B 17/151; A61B 17/157
See application file for complete search history.

(56) References Cited

U.S. PATENT DOCUMENTS 5,059,037 A * 10/1991 Albert ................ F16C 29/0604
384/45
5,364,402 A * 11/1994 Mumme .............. A61B 17/157
606/88
(Continued)

FOREIGN PATENT DOCUMENTS

WO WO-2013179142 A1 12/2013
WO WO-2015003284 A2 1/2015

OTHER PUBLICATIONS

TTA-2 3D Tibial Tuberosity Advancement—Kyon [Retrieved from internet on Apr. 20, 2015] (2015) <URL: https:/web.archive.org/web/*/http://www.kyon.ch/current-products/tibial-tuberosity-advancement-tta/tta-2 development-technique> published Jan. 19, 2015 as per Wayback Machine.
(Continued)

*Primary Examiner* — Nicholas W Woodall
(74) *Attorney, Agent, or Firm* — Harness, Dickey & Pierce, P.L.C.

(57) ABSTRACT

The invention relates to a surgical guide for receiving and guiding a surgical instrument, the guide including; an elongate body extending from a proximal end to a distal end, the elongate body including at least one aperture for receiving and guiding the surgical instrument; at least one positioning mechanism, the positioning mechanism adapted to be directly or indirectly connected to the body and adapted to engage or abut an anatomical location of a patient on which the guide is to be used. The guide is particularly useful in aiding canine tibial tuberosity advancement procedures.

22 Claims, 7 Drawing Sheets

(51) Int. Cl.
 A61B 17/60 (2006.01)
 A61B 17/64 (2006.01)
 A61B 90/11 (2016.01)
 A61D 1/00 (2006.01)
 A61B 17/34 (2006.01)
(52) U.S. Cl.
 CPC .......... *A61B 17/3403* (2013.01); *A61B 17/60* (2013.01); *A61B 17/64* (2013.01); *A61D 1/00* (2013.01); *A61B 2017/3411* (2013.01)

(56) References Cited

U.S. PATENT DOCUMENTS

| | | | | |
|---|---|---|---|---|
| 6,468,280 | B1* | 10/2002 | Saenger | A61B 17/155 606/102 |
| 7,329,260 | B2* | 2/2008 | Auger | A61B 17/155 606/88 |
| 7,887,542 | B2* | 2/2011 | Metzger | A61B 17/155 606/87 |
| 8,475,462 | B2* | 7/2013 | Thomas | A61B 17/151 606/87 |
| 9,023,053 | B2* | 5/2015 | Metzger | A61B 17/155 606/87 |
| 2006/0200158 | A1* | 9/2006 | Farling | A61B 17/155 606/87 |
| 2007/0118138 | A1* | 5/2007 | Seo | A61B 17/154 606/87 |

OTHER PUBLICATIONS

Samoy, Y. et al., TTA Rapid Surgery Instructions, Rita Leibinger Medical, published Nov. 19, 2014, [retrieved from internet on Apr. 20, 2016] <URL:http;//www.ttarapid.com/sites/default/files/TTA%20Rapid%20%20surgery%20Instruction%20%2b%20Patella%29Luxation%2020112014_0.PDF>.

* cited by examiner

SURGICAL GUIDE

CROSS REFERENCE TO RELATED APPLICATIONS

This application is a U.S. National Phase Application under 35 U.S.C. 371 of International Application No. PCT/NZ2016/050009 filed on Feb. 5, 2016 and published in English as WO 2016/126168 on Aug. 11, 2016. This application is based on and claims the benefit of priority from New Zealand Patent Application No. 704592 filed Feb. 5, 2015. The entire disclosures of all of the above applications are incorporated herein by reference.

FIELD OF INVENTION

This invention relates to a surgical guide. More specifically, the invention relates to a surgical osteotomy and drill guide that may be used in canine tibial tuberosity advancement and other orthopaedic or surgical procedures.

BACKGROUND TO THE INVENTION

Tibial tuberosity advancement (TTA) procedures are performed to treat deficient cranial cruciate ligaments in dogs. Currently used TTA procedures include the TTA Rapid™ procedure developed by Rita Leibinger Medical. This procedure allows an osteotomy to be made through a section of the proximal tibia allowing the tibial tuberosity to be advanced outwardly, the advanced tuberosity then held in position using a corresponding tibial tuberosity implant, typically in the form of a wedge. Such advancement of the tibial tuberosity stabilises the stifle joint by changing the angle of the patella ligament, and reducing tibiofemoral shear forces during weight bearing.

The TTA Rapid procedure includes the use of a saw and drill guide to assist the surgeon in correctly positioning the tibial osteotomy, allowing a first pin or drill guide to be inserted at the base of the osteotomy and a second pin at the top of the osteotomy at the proximate end of the tibia. Using this guide, the length of the osteotomy can be controlled and be reproduced exactly over a large number of surgeries. The angle of the osteotomy is typically an oblique angle from the longitudinal axis of the tibia and when using known saw guides, this angle is estimated each time the saw guide is positioned. By having to estimate the angle at which to place the drill guide, it is not possible to reproduce a successful surgery on further patients, and leaves the surgeon open to errors in judgement when placing the guide.

An osteotomy performed at an incorrect angle may result in patellar luxation, corresponding implants not having an optimal fit within the space provided, or may affect the degree to which the tuberosity is able to be advanced, as well as potentially jeopardising the long term success of the TTA operation.

The lack of consistency in the obliquity of the TTA osteotomies also makes it difficult to identify a full set of location parameters of the required osteotomy that may be reproduced across a range of animals.

OBJECT OF THE INVENTION

It is an object of the invention to provide a surgical guide that provides a set of parameters for guiding tibial osteotomies and drill placement in TTA procedures.

Alternatively, it is an object to provide a surgical guide that allows a surgeon to determine placement of a surgical instrument with respect to a patient's anatomical features.

Alternatively, it is an object of the invention to at least provide the public with a useful choice.

SUMMARY OF THE INVENTION

According to a first aspect of the invention, there is provided a surgical guide for receiving and guiding a surgical instrument, the guide including;
 an elongate body extending from a proximal end to a distal end, the elongate body including at least one aperture for receiving and guiding the surgical instrument;
 at least one positioning mechanism, the positioning mechanism adapted to be directly or indirectly connected to the body and adapted to engage or abut an anatomical location of a patient on which the guide is to be used.

In preferred embodiments of the invention one of the one or more apertures is elongate and extends along a portion of the length of the body.

In further preferred embodiments, the elongate aperture is in the form of a channel extending from proximate or at the proximal end of the elongate body to proximate or at the distal end of the elongate body.

Preferably, the channel is intersected by one or more cylindrical apertures having a diameter larger than the width of the channel, the cylindrical aperture being capable of receiving a pin, drill bit or needle.

Preferably the channel runs between a first cylindrical aperture located at or near the proximal end of the elongate body and a second cylindrical aperture located at or near the distal end of the elongate body.

More preferably, the channel is intersected by at least two cylindrical apertures.

More preferably, the channel is intersected by between five and eight cylindrical apertures. In still more preferred embodiments, the channel is intersected by a first cylindrical aperture located at or near the proximal end of the channel between four and seven further cylindrical apertures spaced apart from each other and located at or near the distal end of the channel.

In one embodiment of the invention the four to seven cylindrical apertures are spaced 5 mm apart.

Preferably, the channel is substantially straight.

Preferably, the body is adapted to receive or comprises at least one securing means for securing the body with respect to the patient.

In further preferred embodiments the elongate body includes an aperture located at the proximal end of the elongate body adjacent the proximal end of the channel, the aperture adapted to receive a securing means.

Preferably, the securing means is a screw, pin, or drill bit.

In preferred configurations, the elongate body is substantially rectangular in cross section.

In alternative embodiments the elongate body may have a cylindrical, square, D or U shaped, triangular or other substantially polygonal cross section.

Preferably the body includes at least one longitudinal recess extending from the proximal end of the elongate body to the distal end of the elongate body, and preferably the at least one recess is located on a face of the elongate body orthogonal to the faces through which the one or more apertures extend.

Preferably, the at least one longitudinal recess has a dovetail cross section.

In preferred embodiments of the invention, the at least one positioning mechanism is received within the longitudinal recess.

More preferably, the at least one positioning mechanism is moveable along the elongate body within the longitudinal recess.

Preferably, the positioning mechanism of the guide includes at least one lug.

Preferably, the positioning mechanism includes two lugs, a proximal lug moveably positioned at or near the proximate end of the elongate body, and a distal lug moveably positioned at or near the distal end of the elongate body.

In preferred embodiments, the at least one lug includes an engagement projection extending from a first face of the lug, the engagement projection adapted to moveably engage with the longitudinal recess of the elongate body. Preferably the first face of the lug opposes the longitudinal recess of the elongate body.

More preferably, the engagement projection has a dovetail cross section and is adapted to moveably engage with a recess having a dovetail cross section on the elongate body.

In preferred embodiments, the at least one lug is adapted to lockingly engage with the elongate body.

Preferably, the at least one lug includes a screw locking mechanism.

Preferably, the at least one lug has a top face and an opposing bottom face, the lug including an alignment projection extending from the bottom face of the lug, the projection adapted to engage or abut an anatomical location of a patient. More preferably, the alignment projection is in the form of a rod, at least a portion of the rod extending away from the face from which it extends.

In alternative embodiments of the invention the positioning mechanism is in the form of one or more lugs, the one or more lugs being fixedly connected to the body at discrete positions.

Preferably, the one or more lugs are connected to the body using a connection means selected from a screw mechanism, press or interference fit connection, lock and key connection or a magnetic connection.

Alternatively, the one or more positioning mechanisms are integrally formed with the body. Preferably the bottom face of the lug is angled or contoured.

In alternative embodiments, the geometry of the bottom face of the lug is patient-specific.

Preferably, wherein the guide includes two lugs, the proximal lug includes an alignment projection extending from a region of the bottom face of the lug distal to the portion of the lug connecting or abutting the elongate body and the distal lug includes an alignment projection extending from a region of the bottom face of the lug proximal to the portion of the lug connecting or abutting the elongate body.

A method for guiding a surgical instrument using the surgical guide above, the method including the steps of;
  a) determining one or more preferred instrument positions on a patient body;
  b) configuring the surgical guide for use by moving the one or more lugs along the elongate body such that the apertures on the elongate body correspond to the one or more preferred instrument positions of (a) when the guide is aligned with an anatomical location on the patient;
  c) aligning the guide with an anatomical location on a patient; and
  d) guiding the surgical instrument through or partially through the at least one aperture for use.

In further embodiments the method includes the further step of securing the guide in position using a securing means.

In preferred embodiments the method is a method for guiding a saw blade during an osteotomy. More preferably, the method is used to guide an osteotomy in a tibial tuberosity advancement procedure in canines.

In preferred embodiments, the surgical instrument is a saw, drill, pin or needle, Further aspects of the invention, which should be considered in all its novel aspects, will become apparent to those skilled in the art upon reading of the following description which provides at least one example of a practical application of the invention.

BRIEF DESCRIPTION OF THE DRAWINGS

One or more embodiments of the invention will be described below by way of example only, and without intending to be limiting, with reference to the following drawings, in which.

DETAILED DESCRIPTION OF PREFERRED EMBODIMENTS OF THE INVENTION

The surgical guide of the present invention will be described further in non-limiting terms below with reference to FIGS. 1-7.

One preferred use for the surgical guide of the current invention is guiding an osteotomy during a canine tibial tuberosity advancement (TTA) procedure. For explanatory purposes the description below will refer the use of the guide when performing a TTA procedure, however this is not intended to be limiting in any way. The surgical guide may be used as a guide for a range of surgical procedures in both animals and humans where a guide is required for drill or pin placement, performing an osteotomy or for guiding any other suitable instrumentation.

Figure 1:
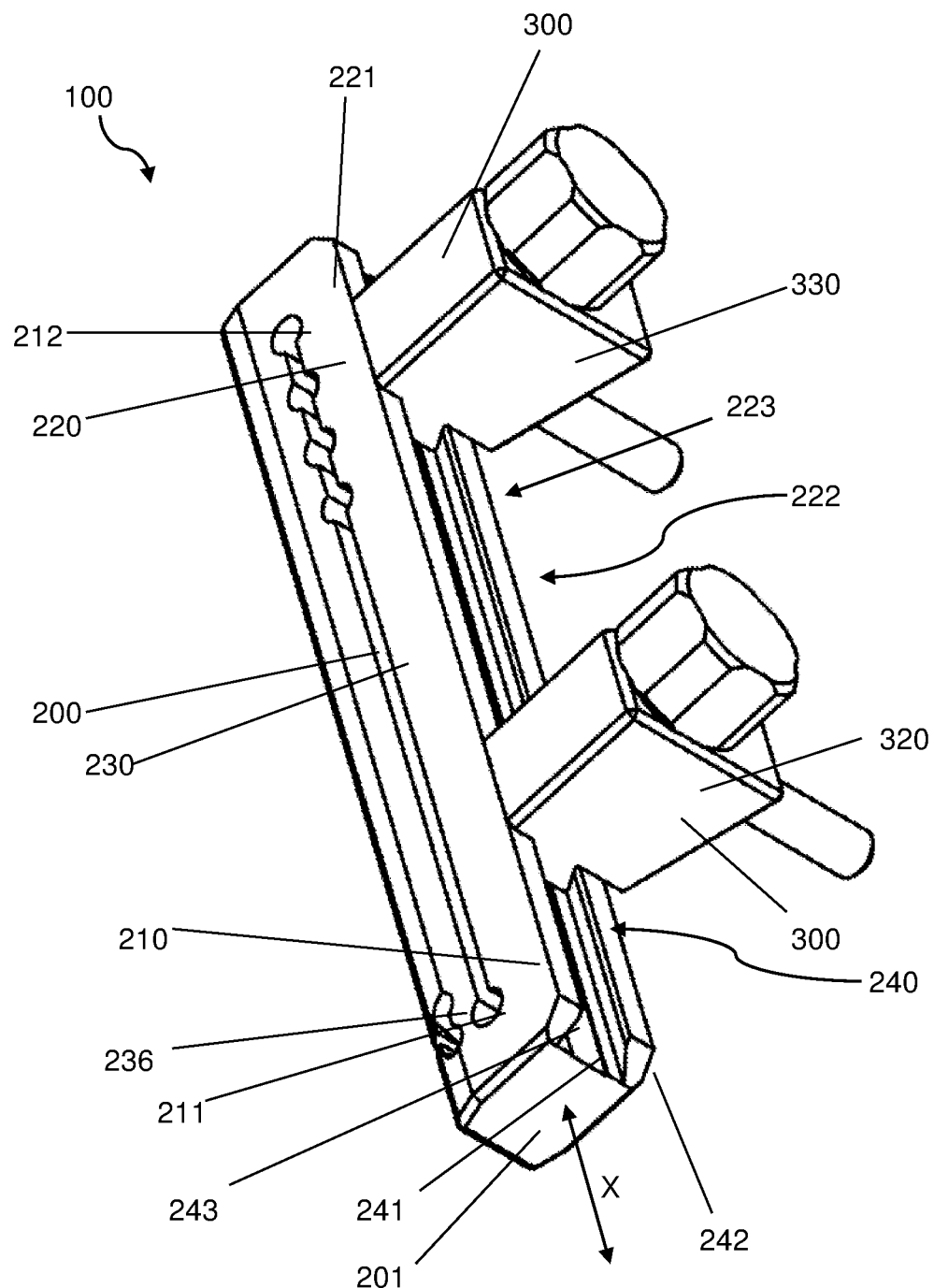
FIG. 1 shows a perspective view of the surgical guide of the present invention in one preferred embodiment.

Guide 100 can be seen in FIG. 1, guide 100 comprising an elongate body 200 and lugs 300. Elongate body 100 is formed with a substantially rectangular cross section indicated at face 201, with edges bevelled to reduce sharp corners. The cross sectional shape of elongate body 200 may take other forms, such as square, triangular, D or U shaped, round, oval, hexagonal or other polygonal shape for example. The cross sectional shape may be chosen to suit a specific surgical location where the guide is intended to be used, and the outer faces of the guide shaped to optimise fit for those specific locations. The cross sectional shape may also incorporate additional flanges or recesses such as those described in further detail below.

Elongate body 200 has a proximal end 210 and a distal end 220. Elongate aperture 230 extends from a top face 221 through the elongate body 200 to a bottom face 222 and is located centrally along the longitudinal axis X of body 200. In preferred embodiments shown, aperture 230 extends from a point 211 proximal the distal end 220 to a point 212 proximal the proximal end 210 of body 200.

Aperture 230 does not extend longitudinally through to the end of the elongate body at either end of the body 200 and body 200 includes blinded ends as seen at both proximal end 210 and distal end 220 of body 200. This configuration of aperture provides a set aperture length to guide a saw blade, so the possibility of over running the osteotomy is prevented. However, in other embodiments it may be more suitable for an aperture to extend completely to one or both ends of the body 200. As would be understood, should a central elongate aperture extend completely through both ends of the body 200, a separate connection means would be required to retain the two sections of the elongate body together.

Aperture 230 is preferably between 0.5 mm-3 mm wide to accommodate a standard oscillating saw blade of 0.6 to 1 mm as may be used in a TTA procedure. The width of aperture 230 may be narrowed or widen as required when formed to suit a particular cutting tool required for a specific procedure. In some embodiments the width of aperture 230 may alter along the longitudinal axis of aperture 230, and the length of the aperture may also be designed as needed for different procedures and different sized guides.

In alternative embodiments there may be more than one elongate aperture positioned on the same longitudinal axis, or there may be two or more elongate apertures of the same or varying widths running parallel to each other along the length of elongate body 200. Depending on the width of body 200, elongate apertures adapted to receive a saw blade or similar may be incorporated at other positions, for example perpendicular to the longitudinal axis of the elongate body, or at a specific angle relative to that axis as needed to perform an osteotomy at a specific anatomical location. The elongate aperture may be substantially straight, or have one or more curved portions.

Figure 2:
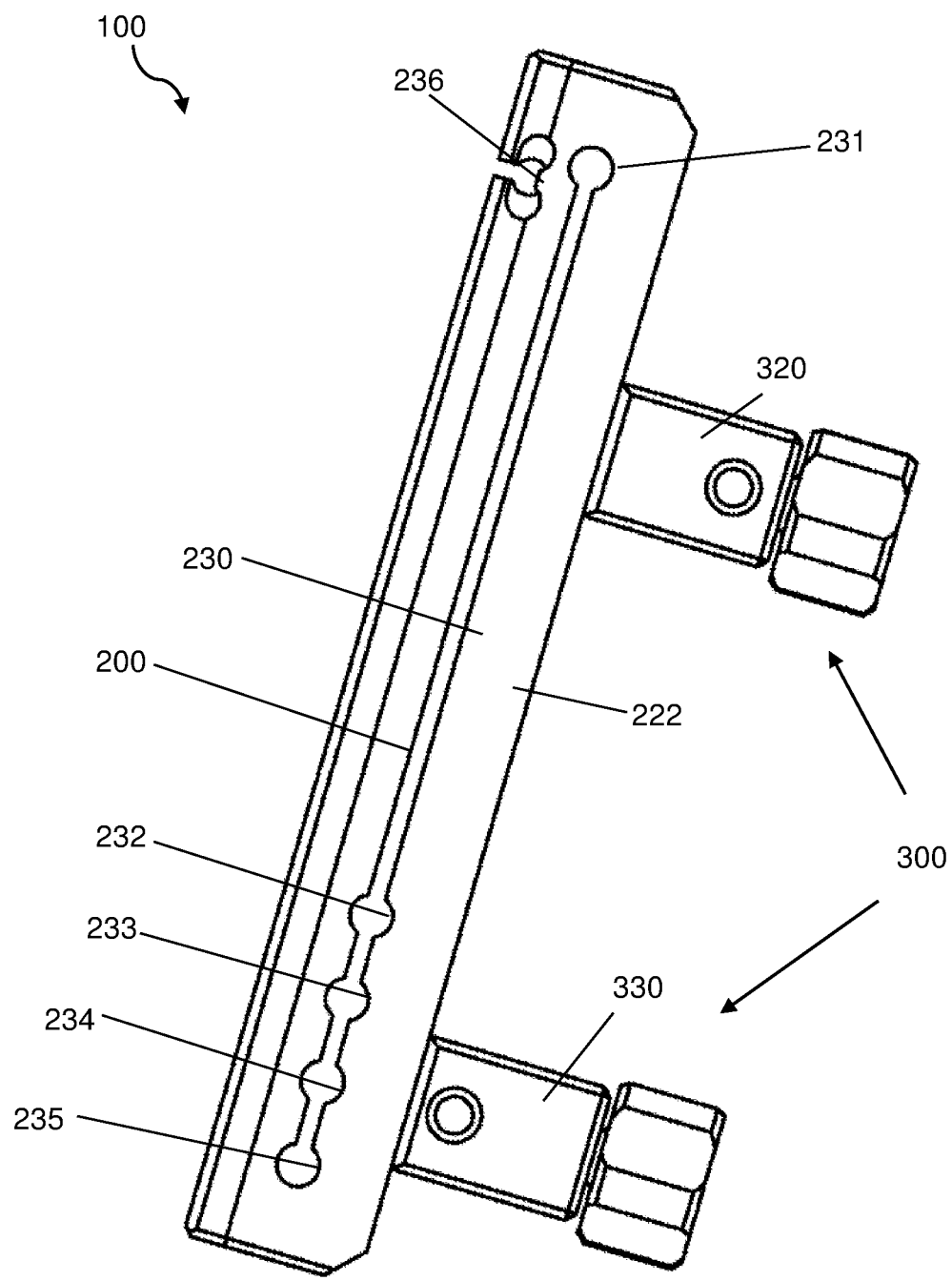
FIG. 2 shows a bottom view of the guide of FIG. 1 showing the lugs and alignment projections.

Aperture 230 can be seen in both FIG. 1 from a top perspective and FIG. 2, shown from underneath the guide, the aperture 230 extending through face 222 of body 200. Elongate aperture 230 is intersected by a first cylindrical aperture 231 at the proximal end of aperture 230. Aperture 231 is dimensioned to receive a drill bit, screw or pin and in preferred embodiments has a diameter of 2.5 mm. Aperture 231 is dimensioned to receive a drill bit and/or screw or pin and aperture 231 extends through the body 200 from the first face 221 to second face 222.

Aperture 231 further acts as an additional guide means for indicating the end of the cutting section defined by aperture 230. Additional cylindrical apertures 232, 233, 234 and 235 are located at the distal end of and intersect with elongate aperture 230. As with aperture 231, apertures 232-235 are dimensioned to receive a drill bit and/or screw or pin and apertures 232-235 extend through the body 200 from the first face 221 to second face 222.

In the embodiment shown in the FIGS. 1-5, apertures 232-235 are spaced 5 mm apart and are positioned 45 mm, 50 mm, 55 mm and 60 mm from the proximal end of the elongated aperture 231. In other alternative embodiments, such as the guide seen in FIG. 6, there may be any number of cylindrical apertures located at the distal end of elongate aperture 230, the size, number and position of which may be altered to be specific to the use for which the guide 200 is designed to be employed. The dimensions required for alternative uses would be clear to a skilled user of the apparatus, for example an orthopaedic or veterinary surgeon. In one alternative embodiment, the elongate body including the four apertures spaced 5 mm apart are located at the proximal end of the elongate body and a single aperture at the distal end, reversing the way the guide may be used.

Figure 6:
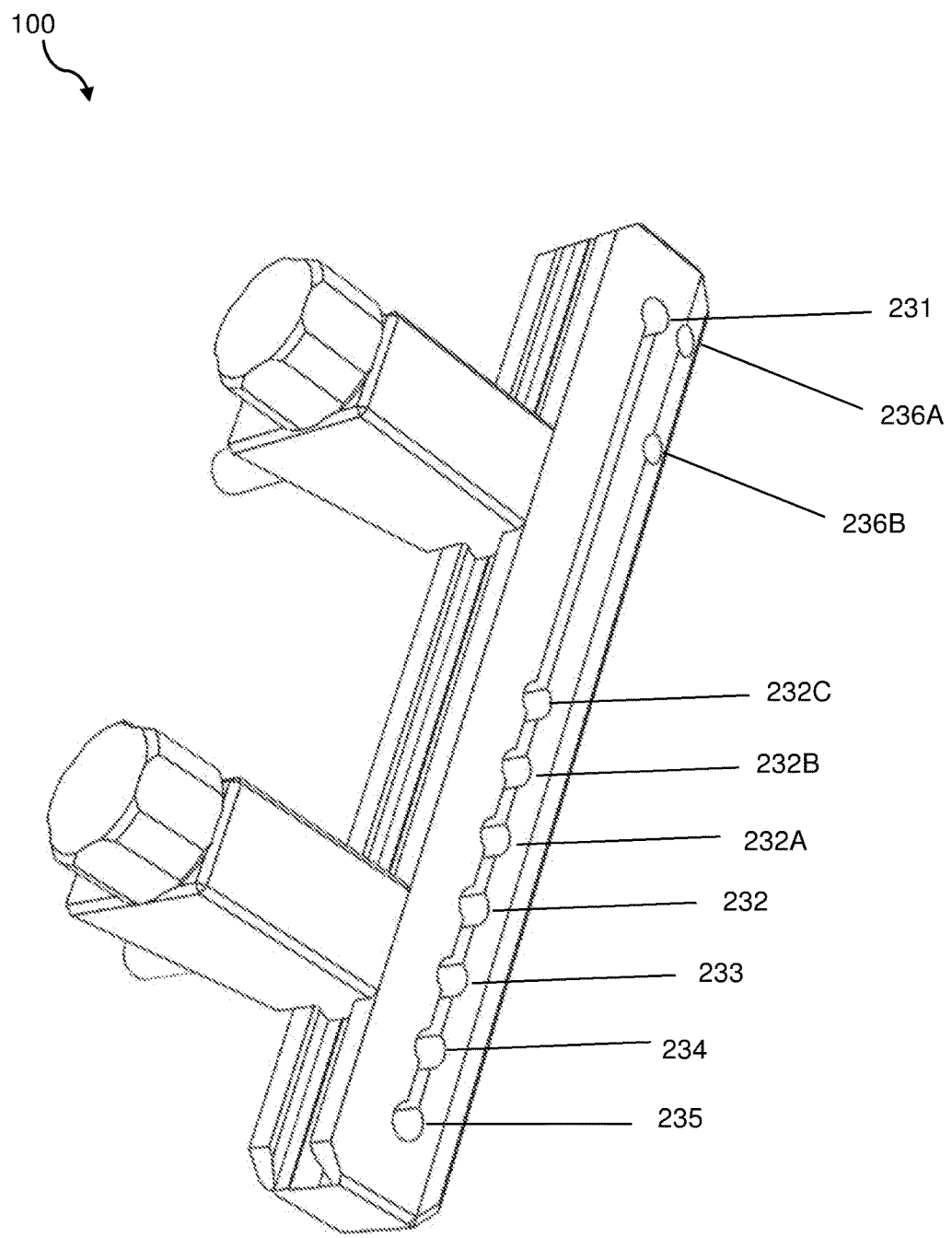
FIG. 6 shows a perspective view of the surgical guide of the present invention in as further preferred embodiment.

A further alternative embodiment can be seen in FIG. 6, where the guide includes additional apertures 232A, 232B and 232C at the proximal end of the guide. This increase in the number of apertures allows for an increased range of positions for receiving the drill bit and/or screw and/or pin.

In the preferred embodiment shown in FIG. 1-5, cylindrical apertures 232-235 are spaced 5 mm apart to correspond to a range of predetermined different size implants that may be fitted during a TTA procedure. As with aperture 231, apertures 232-235 may act as both a guide means for indicating the end of the cutting section defined by aperture 230 and/or may provide a guide in which to secure or insert a drill bit, screw or pin for securing the guide to the patient's body.

Additional aperture 236 is located at the proximate end of elongate body 230 and aperture 236 extends towards and meets the edge of elongate body 200. Aperture 236 may take any shape and is designed to act as a guide for an additional fixation point to secure guide 200 to a patient's body using for example, a pin. In the embodiment shown, aperture 236 includes two cylindrical apertures intersecting each other in X configuration, the X configuration also including a central cylindrical aperture, such that the opening of the aperture 236 at faces 221 and 222 of elongate body 200 are peanut shaped. This configuration of aperture allows a pin, screw or drill bit to be inserted at a number of different angles through aperture 236.

In alternative embodiments as seen in FIG. 6, apertures 236A and 236B act as fixation points as an alternative to the X shaped aperture 236. 236A and 236B are separate cylindrical apertures, allowing more than one securing means into the bone to secure the proximal aspect of the device. These apertures may be at an oblique angle to each other or parallel with each other.

It is envisaged that any number of additional apertures may be formed in the elongate body to allow the user to guide a surgical instrument to a correct position in a patient. The size, shapes and locations of apertures described above are intended to reflect a preferred embodiment for a TTA procedure and are in no way intended to be limiting.

In other embodiments not shown, elongate body 200 may include additional securing means located on the outer surface of the elongate body 200, particularly on face 222, in order to secure the guide in position on a patient body, or to reduce a likelihood of the guide slipping or moving during use. Such features my include, but are not limited to raised ridges, projections or flanges on the bottom face 222, roughened surface textures that increase grip, additional apertures for receiving pins or other securing means, or small hooks or teeth that may connect to the surface on which body 200 is positioned.

Figure 3:
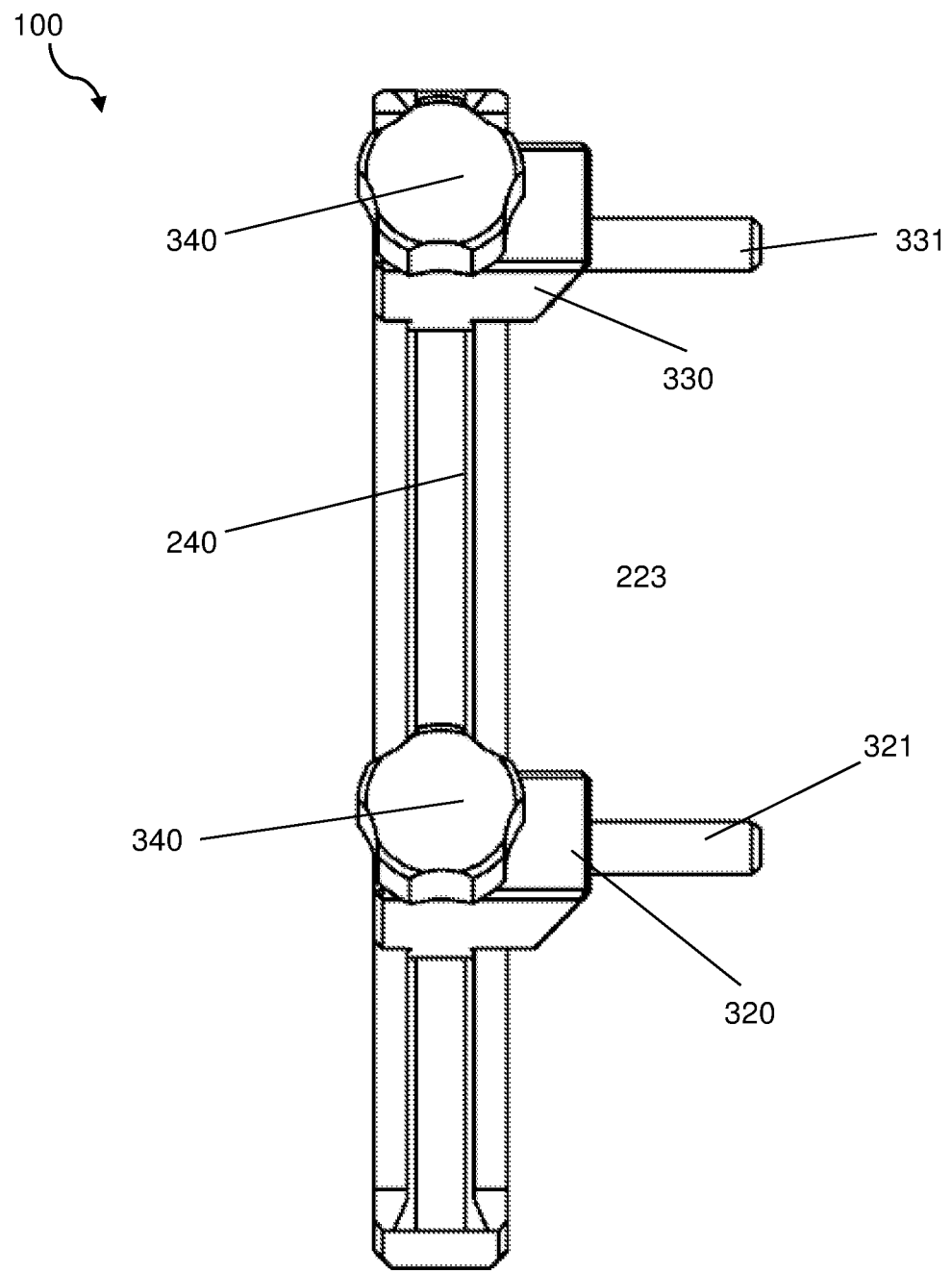
FIG. 3 shows a top view of the guide of FIGS. 1 and 2.

As shown most clearly in FIGS. 1 and 3, elongate body 200 is adapted to receive a positioning mechanism by way of longitudinal recess 240, recess 240 extending from the proximal end 210 of the elongate body 200 to the distal end 220 of the elongate body 200. Recess 240 is located on side face 223 of the elongate body orthogonal to the faces 221 and 222 through which the aperture 230-235 extends.

Recess 240 has a dove tail cross section, the base 241 of the dovetail recess 240 created from side face 223 with inside edges of walls 242 and 243 angled inwardly towards each other to form the angled edges of the dove tailed recess. Recess 240 is adapted to receive an engagement projection 310 of a lug 300 in a dovetail joint arrangement which will be discussed in further detail below in reference to FIGS. 4 and 5.

Recess 240 maintains a consistently sized cross section throughout the length of recess 240, allowing engagement projection(s) 310 to move smoothly up and down the recess 240.

In the preferred embodiment shown, recess 240 extends along the entire face 223 of elongate body 200. In alternative embodiments not shown elongate body 200 may include a number of recesses placed at discrete positions to allow attachment of a lug at specific locations only. Alternatively, elongate body 200 may be adapted to receive a positioning mechanism (such as lug 300) in any number of other ways not shown, for example by inclusion of a rail or flange extending from a face of the body 200, using a friction or interference fit mechanism, one or more clips or hooks to which a positioning mechanism will be adapted to interlock with, receive or be received by.

Figure 4:
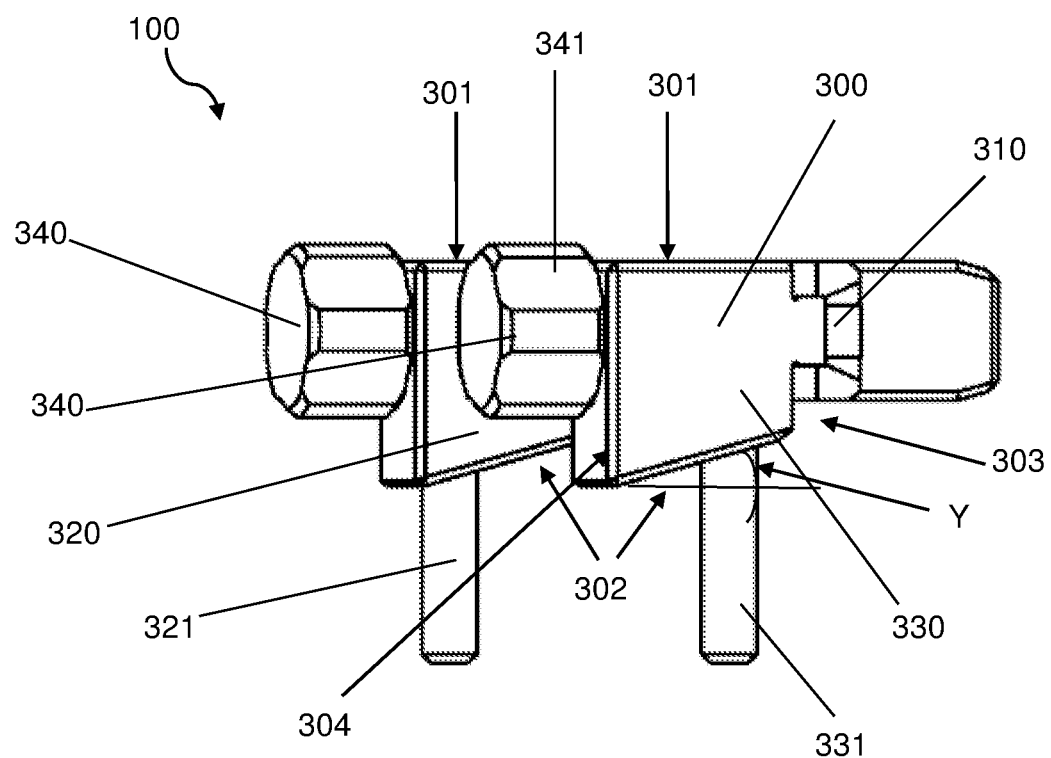
FIG. 4 shows an end perspective view of the surgical guide of FIGS. 1 to 3.
Figure 5:
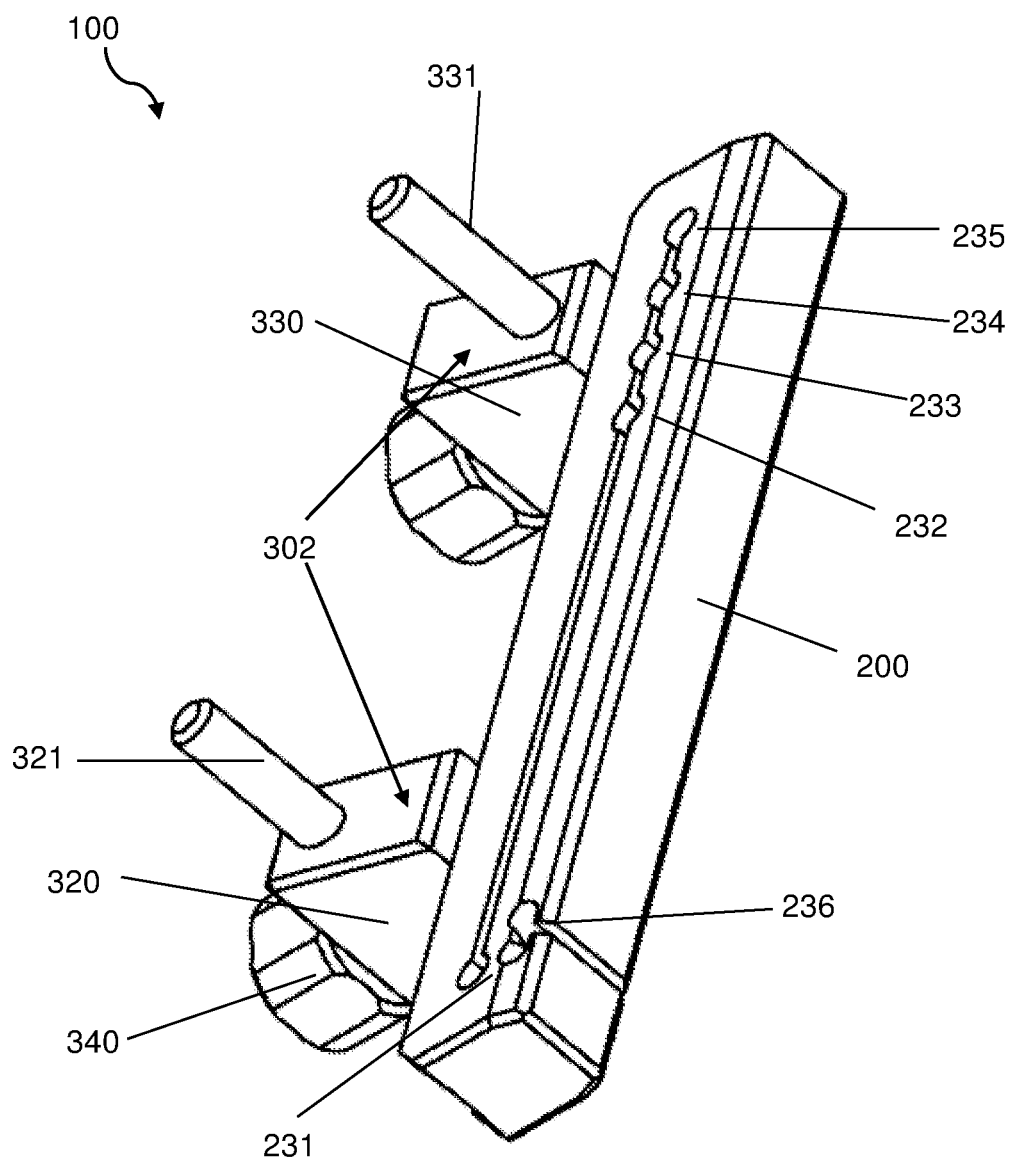
FIG. 5 shows a bottom perspective view of the guide of FIGS. 1-4.

Guide 100 includes two positioning mechanisms 300 in the form of proximal lug 320 and distal lug 330 as seen most clearly in FIGS. 4 and 5. Lugs 320 and 330 have a substantially cuboid form, with bevelled or chamfered edges to reduce sharp edges that may cause damage to the patient during a surgical procedure. Lugs 320 and 330 include a top face 301 and bottom face 302.

Lugs 320 and 330 include an engagement projection 310. Engagement projection 310 extends from faces 302 of each of lugs 320 and 330 and projection 310 is dimensioned to engage with recess 240 of elongate body 200. In this embodiment projection 310 is in the form of a flange having a dovetail shaped cross section, dimensioned such that projection 310 is moveably received within recess 240 which has a corresponding dovetail shaped recess. Together, projection 310 and recess 240 act as a mortise and tenon joint, securing the projection means 320 and 330 to elongate body 200. Lugs 320 and 330 are slideable along recess 240 and may be secured or locked in an exact position along recess 240 using locking mechanism 340.

The cross sectional shape of both projection 310 and recess 240 may be altered, particularly to incorporate other well-known mortise and tenon joint shapes, provided they are able to secure lugs 320 and 330 to the elongate body 200 and projection 310 is securable at specific positions within recess 240.

Locking mechanism 340 is in the form of a screw (not shown) extending from outer face 304 of lugs 320 and 330, through an aperture (not shown) in each lug 320 and 330 and corresponding projection 310. Screw head 341 is sized to allow finger tightening or releasing of the screw by a user.

Other variations in locking screw mechanism not shown include spring, ratchet, friction fit or magnetic locking mechanisms as would be apparent to a person skilled in the art.

Positioning mechanism 300 may be take other forms, such as flanges, tabs or knobs for example, and may be adapted to be moveably or fixably connected to elongate body 200. The guide of the present invention may include one positioning mechanism, or may include two or more positioning mechanisms depending on the required purpose. Positioning mechanisms may vary in size and shape within a single instrument.

Figure 7:
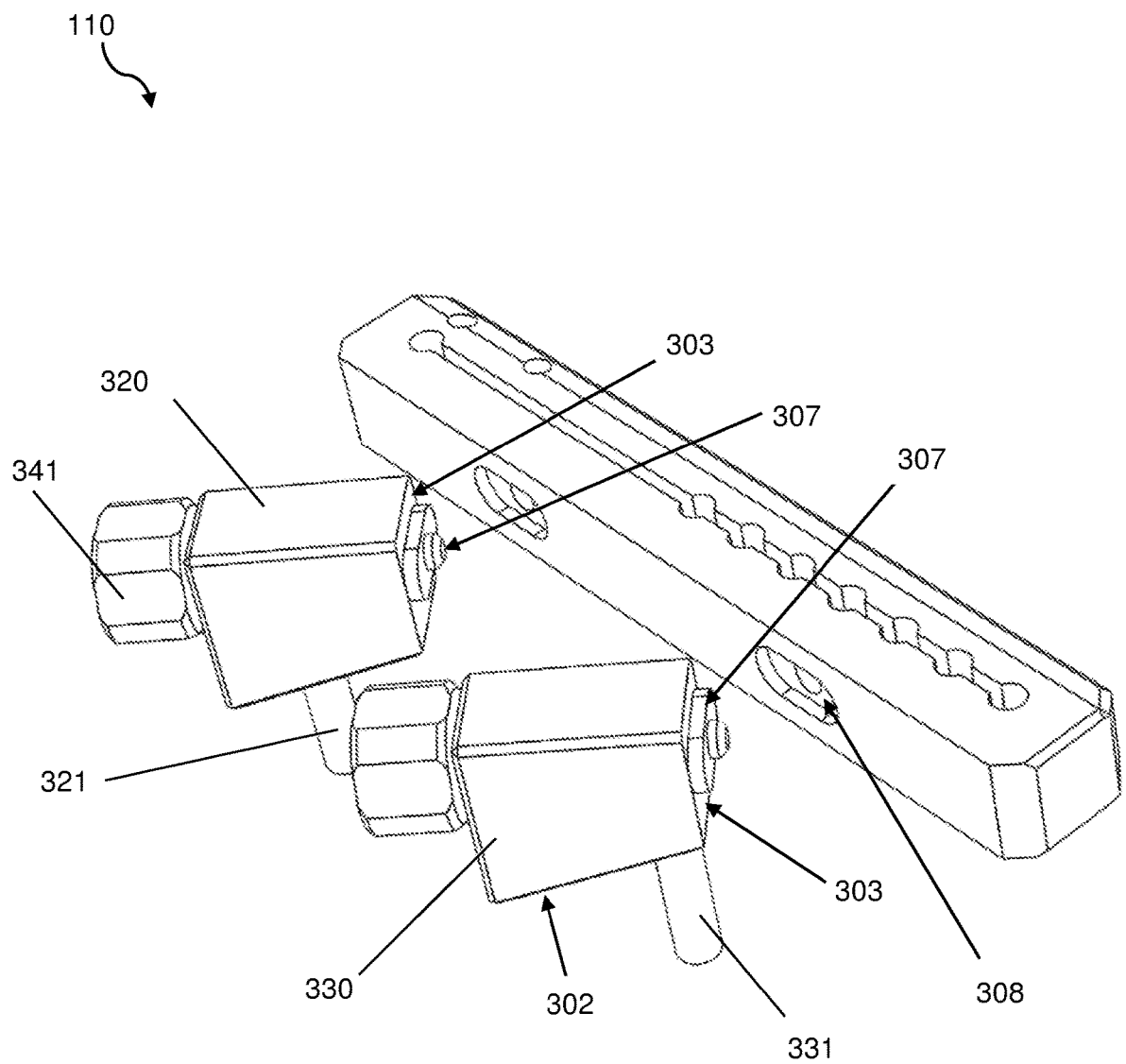
FIG. 7 shows a perspective view of the surgical guide of the present invention in an alternative embodiment of the invention.

FIG. 7 shows an alternative embodiment of the invention in the form of guide 110, wherein recess 240 as shown in the earlier figures is replaced by two female connection points 308 that are adapted to receive two corresponding male projections 307, extending from the face 303 of lugs 320 and 330.

In this alternative embodiment the positioning mechanisms are in a fixed position and are connected to body 200 using a screw locking mechanism 341. It is envisaged that a range of other connection means may also be used, as would be clear to a person skilled in the art, for example friction fit connection means, magnetic connectors, or the one or more positioning means may be integrally formed with the body 200. The connection means may also be reversed from that shown in FIG. 7, with a female connection means located on the positioning mechanism and a male connection means on the body 200.

In variations not shown, the positioning mechanism may be adapted to rotate relative to the elongate body. Rotation around the longitudinal axis X and rotation around an axis Z perpendicular to the longitudinal Y axis would allow the positioning mechanism to move in a multitude of different directions. This adaptation would be particularly useful when the guide is to be positioned in an anatomically complicated region, where there may be a number of projections, ridges, grooves or generally undulating surfaces on the patient's body where the guide is to be positioned.

Corresponding engagement mechanism 310 may also take other forms in any number of other ways not shown, for example by inclusion of a rail or flange extending from a face of the lug 300, one or more clips or hooks, or lock and key mechanism to which elongate body 200 will be adapted to interlock with, receive or be received by. As will be appreciated by a person skilled in the art, any alternative embodiments or forms that may be taken by the positioning means will need to be reflected in how elongate body 200 is adapted to receive, or be received by the positioning means.

Bottom face 302 of lugs 320 and 330 are angled upwardly towards face 303 to provide a suitable resting surface for lugs 320 and 330 to rest on a patient's body when the guide is in use. Angle Y in the preferred embodiment shown has been designed such that it provides the optimum alignment of the guide when used in a TTA procedure, providing a surface to abut against a portion of the tibia on which the guide is being used. This angle may change as required when the guide is being designed for alternative procedures. Bottom face 302 may also include ridges, grooves or a textured surface that will increase the friction between the guide and patient body, making the guide more secure in use and less likely to slip.

In some embodiments, bottom face 302 may have a patient-specific contour, such that the lugs can directly match the surface contours of the patient's body.

Proximal lug 320 and distal lug 330 each include alignment projections 321 and 331 respectively. Alignment projections 321 and 331 are in the form of cylindrical rods extending downwardly at right angles outwardly from face 302. Rods 321 and 331 are approximately 10 mm in length and 3 mm in diameter, although this is not intended to be limiting. Alignment projections 321 and 331 may take any number of forms or shapes, provided they extend from the one or more positioning mechanisms to allow guide 100 to be accurately aligned with an anatomical location on the patient body.

In the preferred embodiments shown in FIG. 2, proximal alignment projection 321 is positioned to extend from face 302 of lug 320 distal from the elongate body 200 and projection 331 is positioned to extend from face 302 of lug 330 proximal to the elongate body. This misalignment of rods 321 and 331 aids in securing the guide 100 in the correct position against a tibia during a TTA procedure. The positioning of the alignment projections may be altered to suit a particular application, and may be parallel to each other, offset, or of differing heights for example. It is envisaged that any number of alignment projections may be incorporated into the guide as required to further stabilise the guide during use.

Alignment projections may be slidable, interchangeable or adjustable with respect to the positioning mechanism from to which they are attached. The alignment means may also include a locking mechanism to fix the alignment means in a set position during a procedure.

The surface of the alignment projections may also include features to aid in securing the guide to a patient, as described above in relation to the lugs and elongate body. In generally, the entire outer surface of guide 100 or parts thereof may include surface characteristics that will help to secure the guide in position on a patient, such as rough or blasted texture, ridges, indents, hooks or grips. In some areas the surface may be polished to assist in correct use of instrumentation.

The guides of the present invention may be manufacture from a range of materials, such as surgical grade stainless steel, plastics, titanium or other metals and metal alloys as would be clear to a person skilled in the art.

Guide 100 of the present invention may be used in a wide variety of surgical and cosmetic applications. The following description refers to the use of the guide as depicted in FIGS. 1 to 5 in a canine TTA procedure.

In a TTA procedure, a tibial osteotomy is performed proximate the tibial tuberosity, and the tuberosity advanced outwardly, allowing a wedge shaped implant to be positioned within the osteotomy. This wedge shaped implant holds the tibial tuberosity in the advanced position, resulting in a stabilised stifle joint.

When using the guide of the present invention to perform this TTA procedure, a TTA implant of a specific size is selected for use depending on the size of the bone and/or patient to which it will be implanted. Typically TTA implants are available in a range of set sizes, and the size most suitable for the patient is selected for use.

Once an implant of a specific size has been selected, guide 100 is set up to guide an osteotomy of the correct length for the implant, and such that the osteotomy is positioned at the most effective angle for a procedure with successful long term results.

Guide 100 includes central elongate aperture 240, adapted to receive a saw blade. Cylindrical apertures 232, 233, 234 and 235 are positioned at a distance from aperture 231 that correspond to the length of osteotomy required for specific implant sizes. For example the distance between aperture 231 and 232 corresponds to the osteotomy size required for the smallest implant available, and the distance between 231 and 235 corresponds to the osteotomy size required for the largest implant available.

Once the implant size has been determined, distal lug 330 is slid along recess 240 until the centre of lug 330 is aligned with a corresponding aperture. For the purposes of explanation, as can be seen in FIGS. 1 and 2, distal lug 330 is aligned with aperture 234, the user having determined that aperture 234 will provide the optimum osteotomy length for the required implant.

Lug 330 is then locked into position opposite aperture 234 using locking mechanism 341. As screw 341 is tightened against face 241 in recess 240 of body 200, dovetailed projection 310 is forced against walls 242 and 243 of recess 240, locking lugs 320 and 330 in position at a set position within recess 240. This locking step ensures that the lug 330 will not move during the osteotomy procedure.

To position proximal lug 320, the user places the guide in position on a patient such that the elongate body 200 rests on the medial face of the proximal tibia, and lugs 320 and 330 with alignment projections 321 and 331 overhang the cranial aspect of the proximal tibia at the insertion point of the patellar ligament on the tibial tuberosity (once the site has been exposed and initial surgical preparations prior to osteotomy have been undertaken) such that proximal aperture 231 is aligned with the most proximal aspect of the tibia within the stifle joint to ensure the osteotomy starts at the proximal aspect of the tibia. To aid correct positioning of this aperture a 2.5 mm pin is placed through aperture 231 to engage the proximal aspect of the tibia.

Once aperture 231 is in position and the proximate end of elongate body 200 is correctly placed, proximal lug 320 is slidably moved along recess 240 such that alignment projection 331 abuts the forward most prominence of the tibia. Lug 320 is then locked in position using the same method as described above for lug 330.

Guide 100 is then gently forced towards the tibia, such that alignment projection 331 and lug 330 abut the tibia. A first drill hole is then made through aperture 234 and the drill bit is either left in place to secure the guide in position on the body, or is removed and replaced with a screw or pin to hold the guide in place. Once the first securing means has been placed, a second securing means may be inserted through aperture 236 at the proximal end of elongate body 200. The second securing means may be inserted directly straight in, or may be inserted at an angle, depending on the shape of the underlying bone. As with the first securing means, a drill hole is made in the aperture, the drill bit either left in position, or replaced with a pin or screw to hold the guide in place at the proximal end.

Guide 100 is now secured in position and the osteotomy can be performed in usual fashion, the surgeon guiding the saw blade from the first end of the elongate aperture 230 as identified by the securing means in aperture 234, through the aperture and underlying bone, until the proximal tibia and/or aperture 231 is reached.

The guide can then be removed and the remaining stages of the TTA procedure completed.

Aligning of the distal lug 330 to match a predetermined implant size and alignment of proximal lug 320 against the tibial tuberosity provides a set angle for the elongate aperture 230 in relation to the outer edge of the tibial bone. The size of the tibial implant is correlated to the size of the tibia in which it is being implanted, therefore, the ability of the guide 100 to adapt to changes in bone size means the osteotomy angles remain substantially uniform with respect to the tibia across the population, regardless of animal size.

This feature is provides a way to reproduce successful surgeries by replicating the same osteotomy parameters between individuals. This eliminates incorrect osteotomy obliquity which causes patellar luxation when the tibial tuberosity is advanced, which when estimated incorrectly, can result in a failure of the procedure. In particular, osteotomies that extend too far along the tibia can compromise and weaken the hinge portion of the bone, which may result in the bone fracturing or the advanced tuberosity snapping off completely. An osteotomy that has too deep an angle may be difficult to wedge open and make implant insertion difficult. Too shallow an angle may result in a thin or unstable tuberosity that may not osseointegrate effectively with the implant, again resulting in the failure of the implant.

The entire disclosures of all applications, patents and publications cited above and below, if any, are herein incorporated by reference.

Reference to any prior art in this specification is not, and should not be taken as, an acknowledgement or any form of suggestion that that prior art forms part of the common general knowledge in the field of endeavour in any country in the world.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

The invention claimed is:

1. A surgical guide for receiving and guiding a surgical instrument, the guide including;
an elongate body extending from a first end to a second end along a longitudinal axis and the elongate body having a length along said axis greater than the width, the first end and second end of the elongate body spaced apart by one or more sides, the one or more sides of the elongate body adapted to simultaneously receive a first positioning mechanism extending outwardly from a first side of the one or more sides in a first direction, and a second positioning mechanism extending outwardly from the first side in the first direction, and the elongate body including at least one aperture in the one or more sides for receiving and guiding the surgical instrument;
two positioning mechanisms, the positioning mechanisms adapted to be simultaneously directly or indirectly connected to a first side of the one or more sides of the elongate body, the first and second positioning mechanisms extending outwardly from the first side of the elongate body in a first direction wherein;
the first positioning mechanism includes a first lug having at least a first side face and a bottom face, the bottom face being at an angle from the first side face, the first side face of the first positioning mechanism directly or indirectly connected to a first side of the elongate body and the bottom face having a first alignment projection extending therefrom; and
the second positioning mechanism includes a second lug having at least a first side face and a bottom face, the bottom face being at an angle from the first side face, the first side face of the second positioning mechanism directly or indirectly connected to a first side of the elongate body and the bottom face having a second alignment projection extending therefrom; such that, in use, the first and second positioning mechanisms engage or abut an anatomical location of a patient.

2. The surgical guide of claim 1, wherein the alignment projection of the first lug is offset from the alignment projection of the second lug relative to the longitudinal axis of the elongate body.

3. The surgical guide of claim 2, wherein the distance of the alignment projection of the first lug from the longitudinal axis of the elongate body further greater than the distance of the alignment projection of the second lug from the longitudinal axis of the elongate body.

4. The surgical guide of claim 3, wherein the alignment projection of the first positioning mechanism extends from a region of the bottom face of the first lug distal to the portion of the first lug connecting or abutting the elongate body and the alignment projection of the second positioning mechanism extends from a region of the bottom face of the second lug proximal to the portion of the second lug connecting or abutting the elongate body.

5. The surgical guide of claim 1, wherein the elongate body includes at least one longitudinal recess extending from at or near the first end of the elongate body to at or near the second end of the elongate body, the at least one longitudinal recess located on a region of the one or more sides of the elongate body orthogonal to a region through which the at least one aperture extends.

6. The surgical guide of claim 5, wherein the positioning mechanisms are received or partially received within the at least one longitudinal recess.

7. The surgical guide of claim 6, wherein the positioning mechanisms are moveable along the elongate body within the at least one longitudinal recess.

8. The surgical guide of claim 5, wherein the positioning mechanisms include an engagement projection extending from the first side face of the first lug and the first side face of the second lug, the engagement projection adapted to moveably engage with the longitudinal recess of the elongate body.

9. The surgical guide of claim 8, wherein the positioning mechanisms are adapted to lockingly engage with the elongate body.

10. The surgical guide of claim 1, wherein the alignment projection is in the form of a rod, at least a portion of the rod extending away from the face from which it attaches.

11. The surgical guide of claim 1, wherein the positioning mechanisms are fixedly connected to the elongate body at discrete positions.

12. The surgical guide of claim 1, wherein the positioning mechanisms are integrally formed with the elongate body.

13. The surgical guide of claim 1, wherein the bottom face of the first and/or second lugs is angled or contoured.

14. The surgical guide of claim 1, wherein the bottom face of one or both lugs is angled or contoured to a patient-specific geometry.

15. The surgical guide of claim 1, wherein the at least one aperture is an elongate aperture in the form of a channel extending from proximate or at the first end of the elongate body to proximate or at the second end of the elongate body.

16. The surgical guide of claim 15, wherein the channel is intersected by one or more cylindrical apertures having a diameter greater than the width of the channel, the cylindrical aperture being capable of receiving a pin, drill bit or needle.

17. The surgical guide of claim 16, wherein the channel runs between a first cylindrical aperture located at or near the first end of the elongate body and a second cylindrical aperture located at or near the second end of the elongate body.

18. The surgical guide of claim 15, wherein the channel is intersected by a first cylindrical aperture located at or near the first end of the channel and four further cylindrical apertures spaced apart from each other and located at or near the second end of the channel.

19. The surgical guide of claim 1 wherein the elongate body is adapted to receive or comprises at least one securing means for securing the elongate body with respect to the patient.

20. The surgical guide of claim 19, wherein the elongate body includes an aperture located at the first end of the elongate body adjacent the end of the channel proximate the first end of the elongate body, the aperture adapted to receive a securing means.

21. A method for guiding a surgical instrument on a patient using the surgical guide as claimed in claim 1, the method including the steps of;
   a) determining one or more preferred surgical instrument positions on the patient body;
   b) configuring the surgical guide for use by moving one or both positioning mechanisms along the longitudinal axis of the elongate body such that the alignment projections of the positioning mechanisms abut the patient at a location such that the at least one aperture on the elongate body corresponds to the one or more preferred surgical instrument positions of a); and
   c) guiding the surgical instrument through or partially through the at least one aperture.

22. The method of claim 21, wherein the method is used to guide an osteotomy in a tibial tuberosity advancement procedure in canines.

* * * * *